United States Patent
Spadgenske

(10) Patent No.: US 7,174,211 B2
(45) Date of Patent: Feb. 6, 2007

(54) HEADER FOR IMPLANTABLE MEDICAL FOR USE WITH BOTH UNIPOLAR AND BIPOLAR LEADS

(75) Inventor: Scott A. Spadgenske, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 651 days.

(21) Appl. No.: 10/274,178

(22) Filed: Oct. 18, 2002

(65) Prior Publication Data

US 2004/0078062 A1 Apr. 22, 2004

(51) Int. Cl.
*A61N 1/375* (2006.01)
(52) U.S. Cl. .......................... 607/36; 607/37
(58) Field of Classification Search ............. 607/36, 607/37, 9; 439/810, 814
See application file for complete search history.

(56) References Cited

U.S. PATENT DOCUMENTS 5,522,861 A * 6/1996 Sikorski et al. ............. 607/36
5,683,433 A * 11/1997 Carson ....................... 607/36
5,720,631 A * 2/1998 Carson et al. ............. 439/668
6,044,302 A * 3/2000 Persuitti et al. ............. 607/37
6,517,476 B1 * 2/2003 Bedoya et al. ............. 600/25

* cited by examiner

*Primary Examiner*—Robert E. Pezzuto
*Assistant Examiner*—Eric D. Bertram
(74) *Attorney, Agent, or Firm*—Nikolai & Mersereau, P.A.; Thomas J. Nikolai

(57) ABSTRACT

The present invention provides a header for an implantable medical device that allows it to be used with either a unipolar lead or a bipolar lead. The set screw normally engaging a ring contact on a bipolar lead is stopped from extending far enough into an insulating layer on a unipolar lead to cause damage to the insulating layer. The use of the universal header of the present invention works to significantly reduce the number of different models of implantable medical devices that a manufacturer must have available.

2 Claims, 5 Drawing Sheets

HEADER FOR IMPLANTABLE MEDICAL FOR USE WITH BOTH UNIPOLAR AND BIPOLAR LEADS

BACKGROUND OF THE INVENTION

I. Field of the Invention

This invention relates generally to the mechanical design of a header for an implantable medical device, such as a cardiac pacemaker or cardiac pacemaker/defibrillator, and more particularly to the design of a header having a lead receiving bore with contacts for mating with either a unipolar lead or a bipolar lead.

II. Discussion of the Prior Art

An implantable medical device typically comprises a metal housing hermetically sealing a battery, a pulse generator circuit and a microprocessor-based controller for the pulse generator such that cardiac stimulating pulses are generated on a timed basis determined by the microprocessor-based controller. Affixed to an exterior wall of the housing is a header for operatively coupling the contacts on the proximal terminals of one or more medical leads to feed-through pins that enter the housing through seals where they connect to circuit inputs and outputs.

The medical leads involved may be unipolar or bipolar. A unipolar lead comprises an elongated flexible, plastic lead body having a conductor running the length thereof for connecting an electrode at a distal end thereof to a contact on a terminal on the proximal end thereof. A bipolar lead will have a distal tip electrode and a ring electrode on the surface of the lead body located proximally of, but close to, the tip electrode. Conductors again run the length of the lead, connecting the tip and ring electrodes individually to a conductive pin and a ring contact on the bipolar lead's proximal terminal.

In the past, manufacturers of implantable medical devices generally offer a plurality of models, each with differing functionality and operating modes. Each such model might be compatible with either a unipolar lead or a bipolar lead, but not both. Thus, if a patient happen to have a unipolar lead implanted, it would be necessary to select a stimulating device having a header that would accept a unipolar lead. If, on the other hand, the patient had a bipolar lead implanted, a model having a header with contacts for mating with the proximal terminal of a bipolar lead would have to be selected.

It should be obvious, then, that if the device manufacturer offered, say, six models of a cardiac stimulating device exhibiting different functionality, it would be necessary to stock 12 different models to assure that each of the six could operate with either unipolar or bipolar leads. This necessarily increases the cost of inventory, and when it is considered that such devices have a limited shelf life, it will frequently happen that units will have to be scraped because of a lack of demand for particular models.

It will be seen, then, that a considerable savings can be realized if a header were designed that could accept either a unipolar lead or a bipolar lead. Unique headers would not have to be made to accommodate the two types of proximal lead terminals in that one such header would work with each type of lead.

It is accordingly a principal object of the present invention to provide a header for an implantable medical device that can accept the proximal lead terminal of either a unipolar or a bipolar lead in a single proximal lead terminal receiving bore.

SUMMARY OF THE INVENTION

In accordance with the present invention, there is provided a header for an implantable medical device where the header has contacts in a lead terminal receiving bore, the contacts being adapted to mate with a proximal terminal of either a unipolar or a bipolar lead. The proximal terminal of the unipolar lead has a proximal pin contact adjacent to a plastic insulating sleeve. The proximal terminal of the bipolar lead has a proximal pin contact and a distal ring contact. The header comprises a plastic body member that is adapted to be affixed to a housing of an implantable medical device. A longitudinal, lead terminal receiving bore is formed in the plastic body member as are first and second longitudinally spaced apertures that extend transversely to and intersect with the bore formed in the body member. First and second conductive connector blocks are respectively placed in the first and second apertures. Each of the connector blocks has a bore concentric with the bore formed in the plastic body member and a threaded bore that extends transverse to and intersects with the bore of the connector block. The bore of the second connector block has a diameter large enough to receive the pin contact of either a unipolar lead or a bipolar lead and the bore of the first connector block has a diameter large enough to receive the distal ring contact of a bipolar lead or the insulating sleeve of a unipolar lead therein. A first set screw is inserted into the threaded bore in the second connector block and is adapted to lock the pin contact of either a bipolar lead or a unipolar lead in the second connector block. Similarly, a second set screw is inserted into the threaded bore in the first connector block and is adapted to engage either the ring contact of a bipolar lead or the insulating sleeve of a unipolar lead. The threads in the threaded bore of the first connector block are such as to preclude the second set screw from damaging the insulating sleeve of the unipolar lead when the second set screw is fully advanced into the threaded bore in the first connector block.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
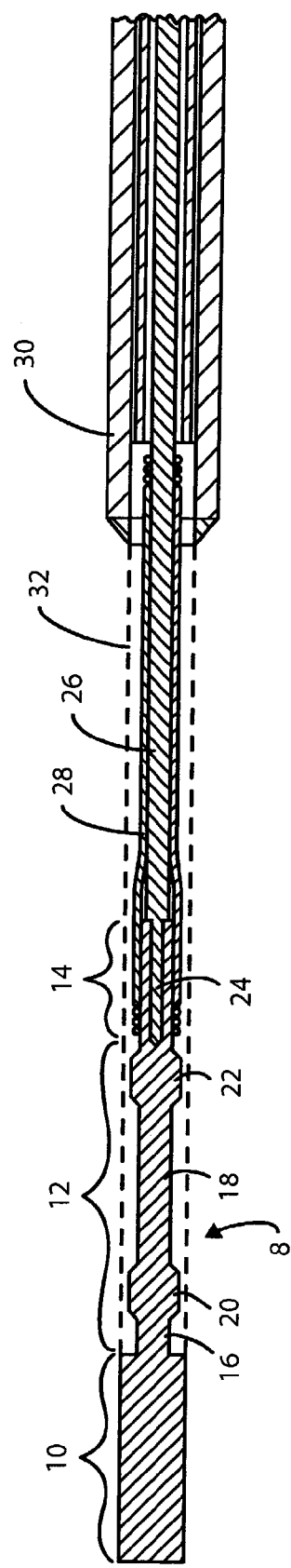
FIG. 1 is a greatly enlarged, side elevation of the proximal terminal portion of a unipolar lead.

Referring to FIG. 1, there is shown a greatly enlarged side elevational view of the proximal terminal portion of a unipolar lead. While the present invention does not pertain to the construction of leads per se, a description of a unipolar lead terminal (FIG. 1) and a bipolar lead terminal (FIG. 2) deemed helpful in understanding the problem solved by the present invention.

Referring to FIG. 1, the unipolar lead includes a conductive metal terminal pin indicated generally by numeral 8 that can be considered as being partitioned into three contiguous zones 10, 12 and 14. In zone 10, the terminal pin 8 is generally cylindrical of a uniform diameter. In zone 12, the pin has reduced diameter portions 16 and 18 that define anchor segments 20 and 22. In zone 14, the pin is tubular and a bore 24 is formed longitudinally therein.

Crimped or otherwise affixed within the lumen of the tubular segment 24 is a core wire 26 that extends the length of the lead and connects to an electrode (not shown) on the distal end of the lead. Wrapped about the outer diameter of the tubular segment 14 is a helically wound wire 28 that also wraps about the core wire 26 where it extends along the length thereof, entering a strain relief member 30.

Covering the terminal pin 8 in zones 12 and 14 and covering the helically wound coil 28 is a layer of elastomeric insulating material, preferably silicon rubber. This sleeve or covering is identified by the dotted lines 32 in FIG. 1. Thus, the only portion of the terminal pin 8 having an exposed metal surface is that identified by bracket 10, the remaining segments thereof being embedded in an insulating sleeve.

Figure 2:
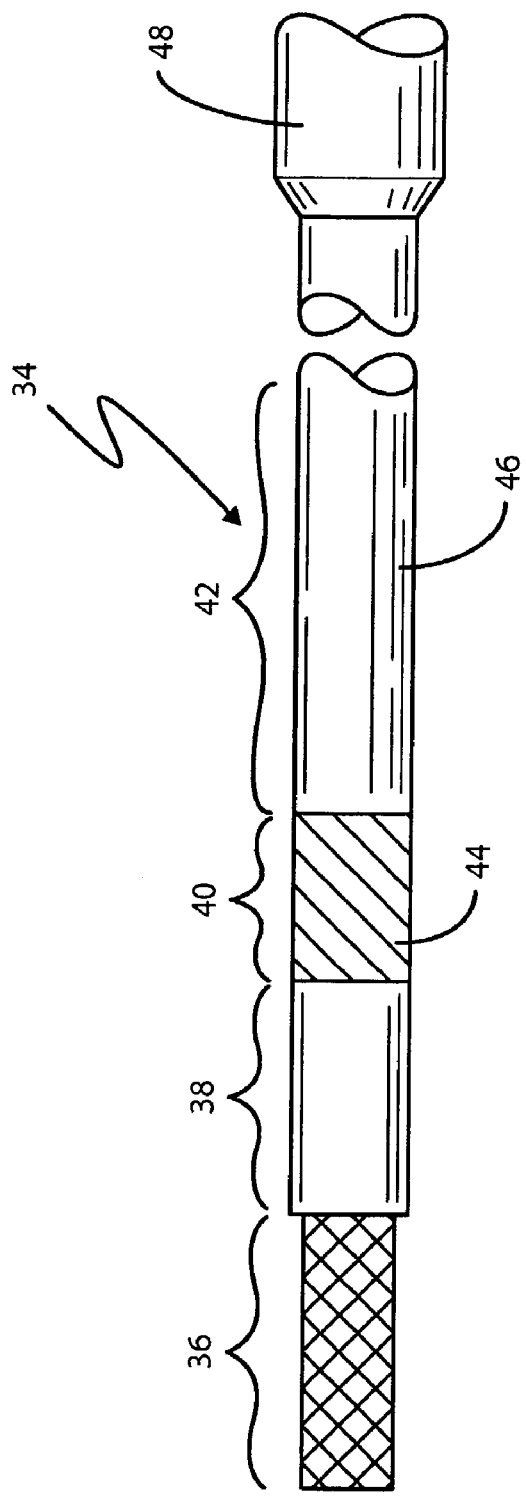
FIG. 2 is a greatly enlarged side elevation of the proximal portion of a bipolar lead.

Referring next to FIG. 2, there is shown a greatly enlarged side elevational view of the proximal terminal of a bipolar lead. It is indicated generally by numeral 34 and can be readily partitioned into four discrete zones identified by brackets 36, 38, 40 and 42. In the zone indicated by bracket 36, the metal of the terminal pin is exposed and it is connected internally by a conductor (not shown) to an electrode at the distal tip of the bipolar lead. In zone 38, this conductor is covered by an insulating plastic, e.g., silicon rubber. Surrounding the silicon rubber layer in the zone indicated by bracket 40 is an annular ring of a conductive metal. A second conductor connects internally to the ring contact 44 and extends the length of the lead where it connects to a ring electrode (not shown) located a predetermined, relatively short distance proximal of the distal tip electrode on the distal end of the lead. The conductors leading to both the terminal pin in zone 36 and the ring contact 44 are insulated from one another and from surface exposure by an insulating sleeve 46 that enters a lumen of a tubular strain relief member 48. The lead terminal 34 has a generally uniform diameter throughout the zones identified by brackets 38, 40 and 42. The exposed terminal pin in the zone enclosed by bracket 36 is of a slightly reduced diameter.

Figure 3:
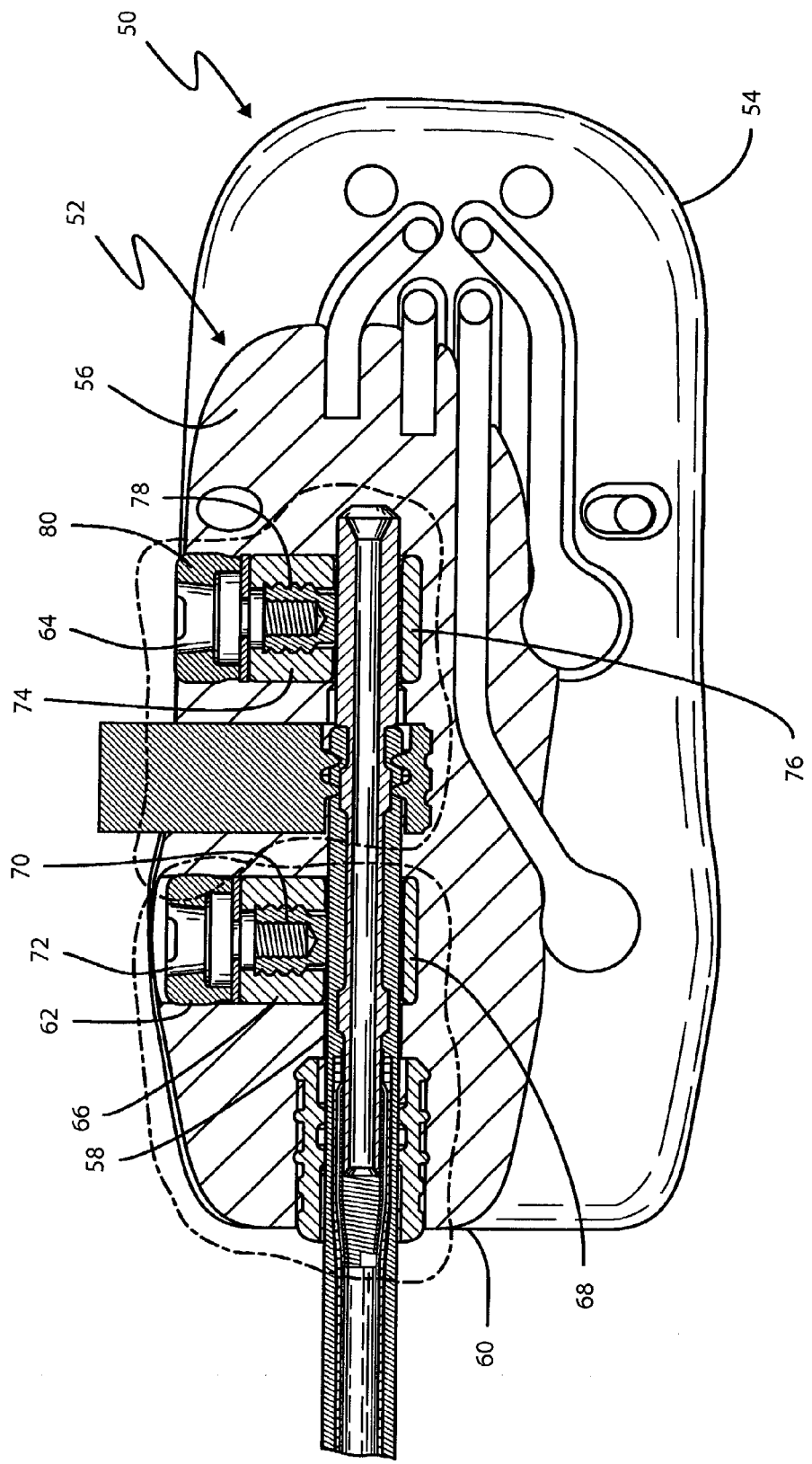
FIG. 3 is a horizontal cross-sectional view taken through the header of an implantable medical device where the header is constructed in accordance with the present invention.
Figure 4:
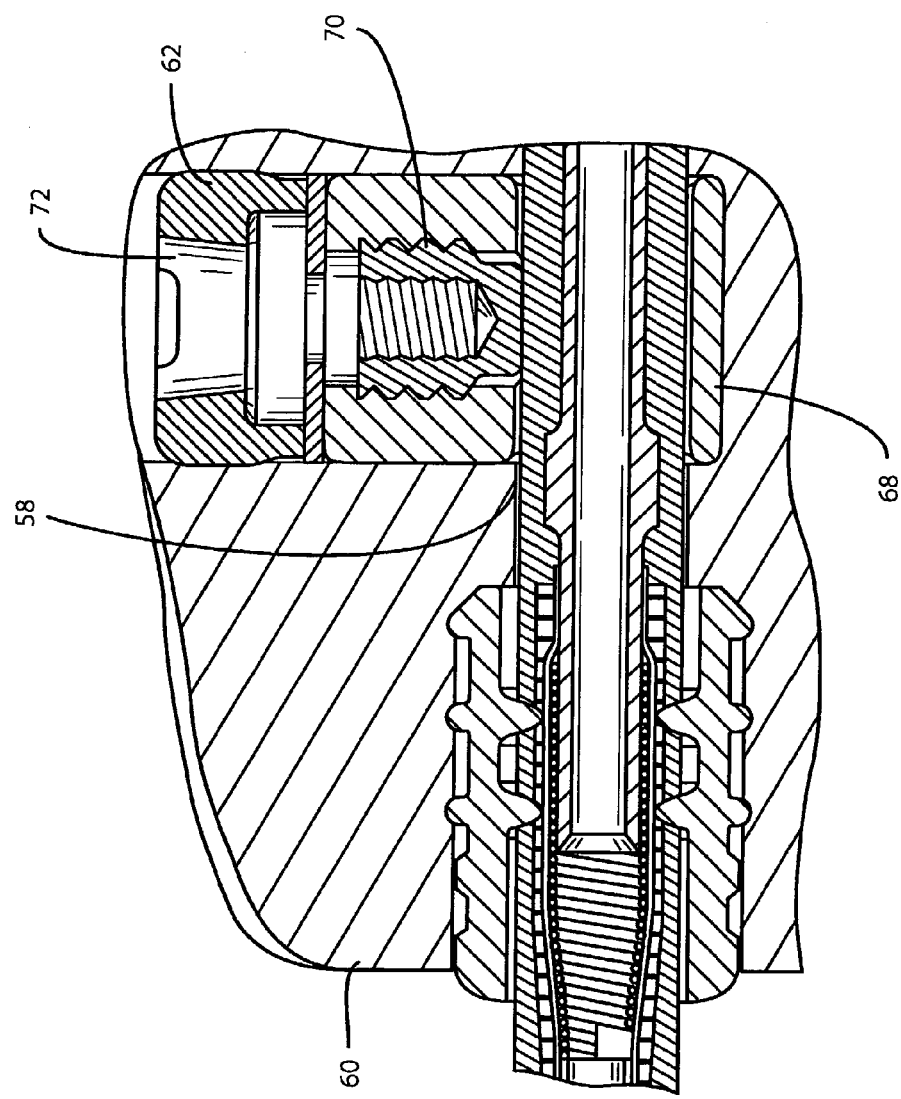
FIG. 4 is an enlarged detailed view of a portion of FIG. 3.
Figure 5:
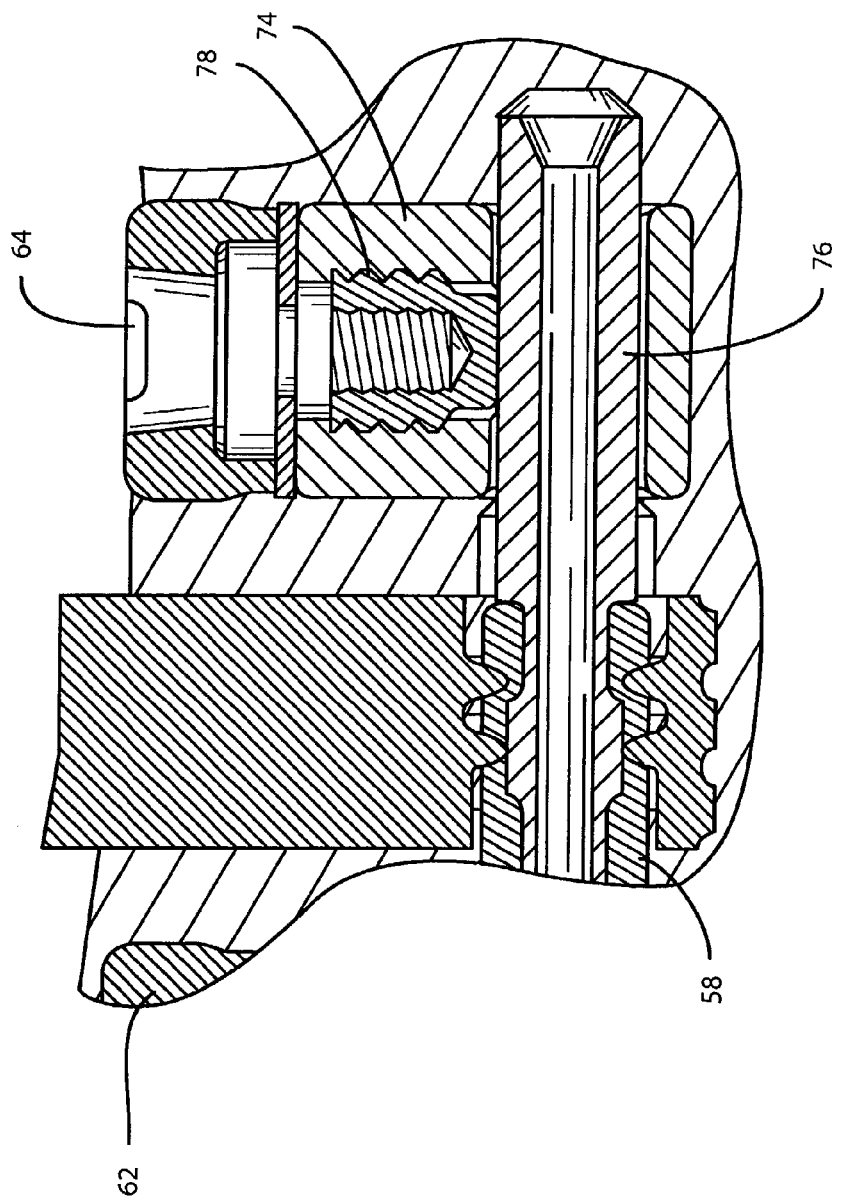
FIG. 5 is an enlarged detail view of a further portion of the cross-sectional view of FIG. 3.

An implantable medical device is indicated generally by numeral 50 in FIG. 3. FIGS. 4 and 5 are detailed views of the portions of FIG. 3 contained within the dotted and dashed lines. It is a top view sectioned horizontally through the device header 52. The implantable medical device 50 includes a housing 54 formed from a suitable metal and preferably titanium. Typically contained within the housing 54 is a battery source of electrical power, a pulse generator circuit and a microprocessor-based controller that controls the time at which cardiac stimulating pulses are generated by the pulse generator.

The header 52 comprises a block of a suitable medical grade plastic 56 having a longitudinal bore 58 formed therein from a front face 60 of the header inward. Also formed in the header block 56 are first and second apertures 62 and 64 that are longitudinally spaced from one another along the length of the bore 58 and which intersect with the bore 58. Inserted into the aperture 62 is a first connector block 66 that is formed from a conductive material. A bore 68 is formed longitudinally through this connector block and it is concentric with bore 58. The connector block 66 further includes a threaded bore 70 that is adapted to receive the threaded shank of a set screw 72 that is insertable into the aperture 62.

The aperture 64 likewise has a second connector block 74 inserted therein. It also has a longitudinal bore 76 formed through it. A threaded bore 78 extends transversely to the bore 76 and intersects the bore 76. A set screw 80 is adapted to be inserted into the aperture 64 and its threaded shank mates with the threaded bore 78.

In order for the header to accept both a bipolar lead and a unipolar lead, it is necessary that the bore in the second connector block 74 be sufficiently large to receive the O.D. of a proximal pin contact of either type of lead and that the set screw can be advanced sufficiently far so that the bottom end of the set screw presses against the proximal pin contact of the lead with sufficient force to press the proximal pin contact against the wall of the bore 64 in the second connector block to effectively lock the two together. The bore 68 in the first connector block must be sufficiently large to receive the distal ring contact of a bipolar lead and the set screw 72 must be able to be advanced until the bottom of the set screw 72 presses against the ring contact with a force sufficient to assure an intimate contact between the distal ring and the bore wall. However, since the insulating sleeve of a unipolar lead also falls within the bore of the first connector block, the set screw 72 must not penetrate so far into the bore 68 that it can cut into the insulating sleeve to thereby compromise its role as an insulator for the proximal pin connector that extends through the insulating sleeve.

In accordance with the present invention, to prevent the set screw used in the first connector block from damaging the insulating sleeve of a unipolar lead connector, a set screw stop is built into the first connector block to limit the extent to which the set screw used in the first connector block may be advanced. While it can be advanced sufficiently far to engage a distal ring contact on a bipolar lead terminal, the stop prevents it from being advanced to the point where it can damage the insulating sleeve on the unipolar lead. The set screw stop is established by the depth to which the bore 70 in the first connector block is tapped with due consideration being given to worse case tolerances of the bipolar lead ring outside diameter and the diameter of the bore 68 formed longitudinally through the first connector block 66.

I have empirically determined that if a connector block serving as the first connector block 66 in the present invention has a bore diameter of 0.0880±0.0015 inch and with a distal ring contact of a diameter of 0.0820±0.0015 inch, an interference fit between the set screw and the distal ring contact of 0.002 inch provides an adequate force to insure a good electrical connection. However, it is important that there be no more than 0.008 inch of interference between the set screw and the silicone insulating sleeve on the unipolar lead when the set screw is turned down all the way if no damage is to occur to the insulation when a unipolar lead is stripped free of the header. This dictates that for a connector block having the center of its longitudinal bore 0.141±0.003 inch from the top edge of the block, the screw stop should be 0.013 inch from the top edge of the block.

It can be seen, then, that by proper attention to dimensional tolerances, a header can be constructed having a lead bore to mate with both a bipolar and a unipolar lead. Accordingly, it is unnecessary to provide unique headers on implantable medical devices to accommodate the two types of lead connectors.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A header for an implantable medical device, the header having contacts in a single lead terminal receiving bore adapted to mate with a proximal terminal of both a unipolar and a bipolar lead, the proximal terminal of the unipolar lead having a proximal pin contact adjacent a plastic insulating sleeve and the proximal terminal of the bipolar lead having a proximal pin contact and a distal ring contact, the header comprising:
   (a) a plastic body member adapted to be affixed to a housing of an implantable medical device;
   (b) a longitudinal, lead terminal receiving bore formed in the plastic body member;
   (c) first and second longitudinally spaced apertures extending transversely to and intersecting with the lead terminal receiving bore formed in the plastic body member;
   (d) first and second conductive connector blocks respectively placed in the first and second apertures, each said connector block having a bore concentric with the lead terminal receiving bore formed in the body member and a threaded bore extending transverse to and intersecting with the bore of the connector block, the bore of the second connector block having a diameter large enough to receive the proximal pin contact of either a unipolar lead or a bipolar lead and the bore of the first connector block having a diameter large enough to receive the distal ring contact of a bipolar lead or the plastic insulating sleeve of a unipolar lead therein;
   (e) a first set screw inserted into the threaded bore in the second connector block and adapted to engage the proximal pin contact of either a bipolar lead or a unipolar lead; and
   (f) a second set screw inserted into the threaded bore in the first connector block and adapted to engage either the distal ring contact of a bipolar lead with an interference fit of at least 0.002 inch or the insulating sleeve of a unipolar lead where the threads in the threaded bore of the first connector block preclude the second set screw from yielding an interference fit greater than about 0.008 inch with the insulating sleeve and thereby damaging the insulating sleeve when the second set screw is fully inserted into the threaded bore in the second connector block.

2. A header for an implantable medical device, comprising:
   (a) a block of insulating material having a lead receiving bore formed inwardly from an edge of the block;
   (b) first and second conductive connector blocks disposed in the lead receiving bore at predetermined longitudinal spacing therebetween, each said connector block including a longitudinal bore generally concentric with the lead receiving bore, the longitudinal bore of the second connector block being of a size adapted to receive a proximal pin terminal of either a unipolar lead or a bipolar lead and the longitudinal bore of the first connector block being sized to receive either a ring contact of the bipolar lead or an insulating sleeve surrounding a portion of the proximal pin terminal of the unipolar lead;
   (c) a threaded bore in each of said first and second conductive connector blocks extending perpendicular to and intersecting with the respective longitudinal bore in the first and second conductive connector blocks, the threads in the threaded bore of the first conductive connector block extending inward from an edge of the first connector block a predetermined distance that is short of the longitudinal bore in the first connector block such that a set screw fully threaded therein engages the ring contact of a bipolar lead with an interference fit of at least 0.002 inch to urge the ring contact against a wall defined by the longitudinal bore in the second conductive connector block when a bipolar lead is used with the implantable medical device and an interference fit of no more than about 0.008 inch with the insulating sleeve of a unipolar lead when a unipolar lead is used with the implantable medical device.

* * * * *